United States Patent
Harrison et al.

(10) Patent No.: US 12,329,758 B2
(45) Date of Patent: Jun. 17, 2025

(54) METHODS FOR THE TREATMENT OF PSORIATIC ARTHRITIS

(71) Applicant: Alfasigma S.p.A., Bologna (IT)

(72) Inventors: Pille Harrison, Juan les Pins (FR); Luc Meuleners, Mechelen (BE); Chantal Thérèse Tasset, Mechelen (BE)

(73) Assignee: ALFASIGMA S.P.A., Bologna (IT)

( * ) Notice: Subject to any disclaimer, the term of this patent is extended or adjusted under 35 U.S.C. 154(b) by 817 days.

(21) Appl. No.: 17/057,946

(22) PCT Filed: May 23, 2019

(86) PCT No.: PCT/EP2019/063283
§ 371 (c)(1),
(2) Date: Nov. 23, 2020

(87) PCT Pub. No.: WO2019/224283
PCT Pub. Date: Nov. 28, 2019

(65) Prior Publication Data
US 2021/0299135 A1    Sep. 30, 2021

(30) Foreign Application Priority Data
May 24, 2018 (GB) ...................... 1808575

(51) Int. Cl.
*A61K 31/541* (2006.01)
*A61P 19/02* (2006.01)

(52) U.S. Cl.
CPC ............ *A61K 31/541* (2013.01); *A61P 19/02* (2018.01)

(58) Field of Classification Search
CPC .................................................. A61K 31/541
See application file for complete search history.

(56) References Cited

U.S. PATENT DOCUMENTS

| | | |
|---|---|---|
| 6,500,854 B1 | 12/2002 | Kitamura et al. |
| 8,088,764 B2 | 1/2012 | Menet et al. |
| 8,242,274 B2 | 8/2012 | Menet et al. |
| 8,563,545 B2 | 10/2013 | Menet et al. |
| 8,853,240 B2 | 10/2014 | Menet et al. |
| 8,999,979 B2 | 4/2015 | Menet et al. |
| 9,284,311 B2 | 3/2016 | van 't Klooster et al. |
| 9,309,244 B2 | 4/2016 | Menet et al. |
| 9,382,247 B2 | 7/2016 | Sabourault et al. |
| 9,415,037 B2 | 8/2016 | Menet et al. |
| 9,707,237 B2 | 7/2017 | Menet et al. |
| 10,206,907 B2 | 2/2019 | Menet et al. |
| 10,328,081 B2 | 6/2019 | Menet et al. |
| 10,376,520 B2 | 8/2019 | Wigerinck et al. |
| 10,493,158 B2 | 12/2019 | De Weer et al. |
| 10,708,263 B2 | 7/2020 | Wigerinck et al. |
| 10,919,890 B2 | 2/2021 | Sabourault et al. |
| 11,000,528 B2 | 5/2021 | Menet et al. |
| 11,667,633 B2 | 6/2023 | Sabourault et al. |
| 12,042,498 B2 | 7/2024 | Menet et al. |
| 2005/0222171 A1 | 10/2005 | Bold et al. |
| 2013/0310340 A1 | 11/2013 | Payan et al. |
| 2013/0345209 A1* | 12/2013 | van 'T Klooster ....... A61P 1/00 514/228.5 |
| 2017/0173034 A1 | 6/2017 | Di Paolo |
| 2018/0263997 A1* | 9/2018 | Alonzo ............... A61K 9/2018 |

FOREIGN PATENT DOCUMENTS

| | | |
|---|---|---|
| EP | 1391211 A1 | 2/2004 |
| EP | 2305673 A1 | 4/2011 |
| EP | 2445911 A1 | 5/2012 |

(Continued)

OTHER PUBLICATIONS

Mease et al, Tofacitinib or Adalimumab versus Placebo for Psoriatic Arthritis, 2017, N. Engl. J. of Med, vol. 377, No. 16, p. 1537-1550. (Year: 2017).*
International Search Report and Written Opinion issued in PCT/EP2019/063283 dated Aug. 22, 2019, pp. 1-13.
Mease P. et al., "Filgotinib, an Oral, Selective Janus Kinase 1 Inhibitor, is Effective in Psoriatic Arthritis Patients with an Inadequate Response to Conventional Disease-modifying Antirheumatic Drugs: Results from a Randomized, Placebo-Controlled, Phase 2 Study", Arthritis & Rheumatology, John Wiley & Sons, Inc., US, vol. 70, No. suppl. 9, Aug. 31, 2018, p. 1821.
Mease P. et al.,"Efficacy and Safety of Filgotinib, a selective Janus kinase 1 inhibitor, in patients with active psoriatic arthritis (Equator): results from a randomised, placebo-controlled, phase 2 trial," Lancet, 2018, vol. 392, No. 10162, pp. 2367-2377.

(Continued)

*Primary Examiner* — Kamal A Saeed
*Assistant Examiner* — Karen Cheng
(74) *Attorney, Agent, or Firm* — Jeff B. Vockrodt; CM Law

(57) ABSTRACT

The present invention relates to compound according to Formula I:

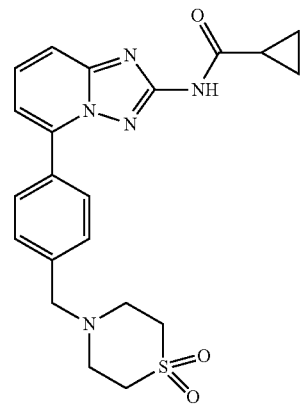

or a pharmaceutically acceptable salt thereof, or a solvate or the salt of a solvate thereof, pharmaceutical compositions comprising the same, and methods of treatment using the same, for use in the treatment of psoriatic arthritis, by administering the compound according to Formula I.

12 Claims, No Drawings

(56) References Cited

FOREIGN PATENT DOCUMENTS

| | | |
|---|---|---|
| EP | 2778159 A1 | 9/2014 |
| JP | 2013049632 A | 3/2013 |
| WO | 2003010167 A1 | 2/2003 |
| WO | 2004039816 A1 | 5/2004 |
| WO | 2004072072 A1 | 8/2004 |
| WO | 2005124342 A2 | 12/2005 |
| WO | 2006018735 A2 | 2/2006 |
| WO | 2006038116 A2 | 4/2006 |
| WO | 2007009773 A1 | 1/2007 |
| WO | 2008025821 A1 | 3/2008 |
| WO | 2008150015 A1 | 12/2008 |
| WO | 2009010530 A1 | 1/2009 |
| WO | 2009017954 A1 | 2/2009 |
| WO | 2009027283 A1 | 3/2009 |
| WO | 2009047514 A1 | 4/2009 |
| WO | 2009155565 A1 | 12/2009 |
| WO | 2010010184 A1 | 1/2010 |
| WO | 2010010186 A1 | 1/2010 |
| WO | 2010010187 A1 | 1/2010 |
| WO | 2010010188 A1 | 1/2010 |
| WO | 2010010189 A1 | 1/2010 |
| WO | 2010010190 A1 | 1/2010 |
| WO | 2010010191 A1 | 1/2010 |
| WO | 2010013768 A1 | 2/2010 |
| WO | 2010149769 A1 | 12/2010 |
| WO | 2013069297 A1 | 5/2013 |
| WO | 2013189771 A1 | 12/2013 |
| WO | 2015117980 A1 | 8/2015 |
| WO | 2016165953 A1 | 10/2016 |

OTHER PUBLICATIONS

Robin-Jagerschmidt C., et al., "The JAK1 selective inhibitor Filgotinib regulates both enthesis and colon inflammation in a mouse model of psoriatic arthritis," Annals of the rheumathic diseases, 2017, vol. 76, No. 2, pp. 118-119.
Argiles 1998 Curr Opin Clin Nutr Metab Care. 1: pp. 245-251.
Bain, J, 2003, biochem J371: pp. 199-204.
Bastin R J: "Salt selection and optimisation procedures for pharmaceutical new chemical entities", Organic Process Research & Development, vol. 4(5), 2000, pp. 427-435.
Berge et al. "Pharmaceutical salts", Jan. 1977, Journal of Pharm. Sciences, vol. 66, N. 1, pp. 1-19.
Berishaj et al., "Stat3 is tyrosine-phosphorylated through the interleukin-6/glycoprotein 130/Janus kinase pathway in breast cancer", Breast Cancer Res., 2007, vol. 9(3), R32.
Bundgard., "Prodrugs as a Means to Improve the Delivery of Peptide Drugs," Adv. Drug Del Rev., vol. 8, 1992, pp. 1-38.
Bush et al., "Reduction of joint inflammation and bone erosion in rat adjuvant arthritis by treatment with interleukin-17 recetor IgGl Fe fusion protein", 2002, Arthritis Rheum., vol. 46, pp. 802-805.
Changelian et al., "The specificity of JAK3 kinase inhibitors", Blood, 2008, vol. 111, pp. 2155-2157.
Chen et al., "Janus kinase deregulation in leukemia and lymphoma", Immunity, 2012, vol. 36, pp. 529-541.
CHMP, Guideline on Clinical Investigation of Medicinal Products indicated for the treatment of Psoriasis, 2004.
Choy et al., "Cytokine pathways and joint inflammation in Rheumatoid Arthritis", N. Engl. J. Med., 2001, vol. 344 (N 12): pp. 907-916.
Chubinskaya et al., "Regulation of osteogenic proteins by chondrocytes", Int. J. Biochem. & Cell Biology, 2003, vol. 35, pp. 1323-1340.
Clegg et al., "Glucosamine, chondroitin sulfate and the two in combination for painful knee osteoarthritis", N. Engl. J. Med., 2006, vol. 354(8), pp. 795-808.
Communication pursuant to Art 94(3) EPC dated May 29, 2024, 5 pages.
Constantinescu et al., "Mining for JAK-STAT mutations in cancer", Trends in Biochemical Sciences, 2007, vol. 33(3), pp. 122-131.

Dolgin et al., "Companies hope for kinase inhibitor JAKpot", Nat Rev Drug Discovery, 2011, vol. 10, pp. 717-718.
Drug Discovery and Development, Understanding the R&D process, Pharmaceutical Research and Manufacturers of America, 2007; pp. 1-14.
Dymock, "Recent News in the Fast-Paced Field of JAK Inhibitors", J Develop Drugs, 2013, vol. 2(2), pp. 1-2.
Fabian et al., "A small molecule-kinase interaction map for clinical kinase ihibitors",Nature Biotech, 2005, vol. 23(3), pp. 329-336.
Firestein, G. S., "Evolving Concepts of Rheumatoid Arthritis", Nature, 2003, vol. 423, No. 6937, pp. 356-361.
First Examination Report received in AU Application No. 2019273664 dated May 14, 2024, 3 pages.
Geron et al., "Selective inhibition of JAK2-driven erythroid differentiation of polycythemia", Cancer Cell, 2008, vol. 13(4), pp. 321-330.
Ingersoll et al., "The impact of medication regimen factors on adherence to chronic treatment: a review of literature", J Behav Med, 2008, vol. 31(3), pp. 213-224.
Ip et al., "Interleukin (IL)4 and IL-13 up-regulate monocyte chemoattractant protein-I", British Society for Immunology: Clinical and Experimental Immunology, 2006, vol. 145, pp. 162-172.
Jou et al., "Thrombospondin 1 as an effective gene therapeutic strategy in collagen-induced arthritis," Arthritis & Rheum, 2005, vol. 1, pp. 339-344.
Kachigian, "Collagen antibody-induced arthritis," Nature Protocols, 2006, vol. 1, No. 5, pp. 2512-2516.
Kopf et al., "Averting inflammation by targeting the cytokine environment", Nat Rev Drug Discov, 2010, vol. 9, pp. 703-718.
Kudlacz et al., "The JAK-3 inhibitor CP-690550 is a potent anti-inflammatory agent in a murine model of pulmonary eosinophilia," Eur. J. Pharmaco, 2008, vol. 582, pp. 154-161.
Labadie, et al., Design and evaluation novel 8-0×0-pyridopyrimidine JAK1/2, Bioorganic & Medicinal Chemistry Letters, 2013, vol. 23, pp. 5923-5930.
Laurence, et al., "JAK Kinases in Health and Disease: An Update", Open Rheumatology Journal, 2012, vol. 6 (2), pp. 232-244.
Lee et al., "Rheumatoid arthritis", Lancet, 2001, vol. 358, pp. 903-911.
Legendre et al., "JAK/STAT but not ERK1/ERK2 pathway mediates interleuking . . . ", J. Biol. Chem., 2003, vol. 278, No. 5, pp. 2903-2912.
Levy et al., "STAT3 Signaling and the Hyper-IgE Syndrome," N. Engl. J. Med., 2007, vol. 357, pp. 1655-1658.
Li et al., "Oncostatin M-induced matrix metalloproteinase and tissue inhibitor of . . . ", J. of Immun., 2001, vol. 166, pp. 3491-3498.
Lin et al., "Anti-rheumatic activities of histone deacetylase (HDAC) inhibitors in vivo in collagen-induced arthritis in rodents," The British J. of Pharma., 2007, vol. 150, pp. 862-872.
Lipinski et al., "Experimental and computational approaches to estimate solubility and permeability in drug discovery and development settings", Advanced Drug Delivery Reviews, 2001, vol. 46, pp. 3-26.
McGinnity et al., "Evaluation of fresh and cryopreserved hepatocytes as in vitro drug metabolism tools for the prediction of metabolic clearance," Drug Metab Disp., 2004, vol. 32, No. 11, pp. 1247-1253.
Milici et al., "Cartilage preservation by inhibition of Janus Kinase 3 in two rodent models of rheumatoid arthritis", Arthritis Research & Therapy, 2008, vol. 10, pp. R14.
Mullighan et al., "JAK mutations in high-risk childhood acute lymphoblastic leukemia", Proc Natl Acad Sci, 2009, vol. 106(23), pp. 9414-9418.
Naka et al., "The paradigm of IL-6: from basic science to medicine", Arthritis Res, 2002, vol. 4, Suppl 3, pp. S233-S242.
Nettekoven et al., "Synthetic Access to 2-Amido . . . ", Synthesis, 2003, vol. 11, pp. 1649-1652.
Nials et al., "Mouse Models of Allergic Asthma: Acute and Chronic Allergen Challenge," Disease Models & Mechanisms, 2008, vol. 1, pp. 213-220.
Nishida et al., "Histone Deacetylase Inhibitor Suppression ," Arthritis & Rheum., 2004, vol. 50, pp. 3365-3376.

(56) References Cited

OTHER PUBLICATIONS

O'Dell, "Therapeutic Strategies for Rheumatoid Arthritis", N. Engl. J. Med, 2004, vol. 350, pp. 2591-2602.
Office Action received in Chinese Application No. 201980034599 dated Jul. 21, 2023, with translation, 9 pages.
Office Action received in Chinese Application No. 201980034599 dated May 8, 2024, with translation, 7 pages.
Office Action received in Japanese Application No. 2020-565417 dated Apr. 25, 2023, with translation, 8 pages.
Office Action received in Japanese Application No. 2020-565417 dated Oct. 17, 2023, with translation, 4 pages.
Osaki et al., "The TAT A-containing core promoter of the type II collagen gene ," Biochem J., 2003, vol. 369, pp. 103-115.
Oshea et al., "A New Modality for Immunosuppresion: Targeting the JAK/STAT Pathway", Nature Rev Drug Disc, vol. 3, 2004, pp. 555-554.
O'Shea et al., "Cytokine Signaling Modules in Inflammatory Responses", Immunity, 2008, vol. 28, pp. 477-487.
O'Shea et al., "JAK and STAT Signaling Molecules in Immunoregulation and Immune-Mediated Disease", Immunity, 2012, vol. 36, pp. 542-550.
Oste et al., "A high throughput method of measuring bone architectural disturbance in a murine CIA model by micro-CT morphometry", ECTC Montreal, 2007.
O'Sullivan et al., "Cytokine receptor signaling through the Jak-Stat-Socs pathway in disease", Molecular Immunology, 2007, vol. 44(10), pp. 2497-2506.
Otero et al., "Signaling pathway involved in nitric oxide synthase type II . . . ", Arthritis Research & Therapy, vol. 7(3), pp. 581-591.
Pernis et al., "JAK-STAT signaling in asthma", J. Clin—Invest, 2002, vol. 109, pp. 1279-1283.
Punwani et al., "Preliminary clinical activity of a topical JAK1/2 inhibitor in the treatment of psoriasis", Journal of the American Academy of Dermatology, 2012, vol. 67(4), pp. 658-664.
Rall et al., "Rheumatoid Cachexia: Metabolic Abnormalities, Mechanisms and Interventions", Rheumatology, 2004, vol. 43, pp. 1219-1223.
Rodig et al., "Disruption of the Jak1 Gene Demonstrates Obligatory and Nonredundant Roles of the Jaks in Cytokine-Induced Biologic Responses", Cell, vol. 93, 1998, pp. 373-383.
Saharinen, et al., "Regulation of the Jak2 Tyrosine Kinase by Its Pseudokinase Domain," Molecular and Cellular Biology, vol. 20, No. 10, 2000, pp. 3387-3395.
Salvemini, "Amelioration of Joint Disease in a Rat Model of Collagen-Induced Arthritis by M40403, a Superoxide Dismutase Mimetic", Arthritis Rheum, vol. 44, No. 12, 2001, pp. 2909-2921.
Seavey, et al., Biochemical Pharmacology, "The many faces of Janus kinase", 2012, vol. 83, pp. 1136-1145.
Shelton, Nerve Growth Factor Mediates Hyperalgesia and Cachexia in Auto-immune Arthritis, Pain, vol. 116, 2005, pp. 8-16.
Sims, "Targeting Osteoclasts With Zoledronic Acid Prevents Bone Destruction in Collagen-Induced Arthritis" Arthritis Rheum., vol. 50, No. 7, 2004, pp. 2338-2346.
Smolen JS, Steiner G., "Therapeutic Strategies for Rheumatoid Arthris", Nat Rev Drug Discov., vol. 2, 2003, pp. 473-488.
SoftFocus SFK Directed Libraries; Library SFK 39, "Serine-Threonine and Tyrosine Kinase directed," BioFocus DPI, Advertising Article, 2006.
Stahl et al., eds., "Handbook of pharmaceutical salts, Properties, selection and use", Wiley-VCH, 2008, pp. 265-327.
Tam et al., "Expression levels of the JAK/STAT pathway in the transition from hormone-sensitive to hormone-refractory prostate cancer", Br J Cancer, 2007, vol. 97(3), pp. 378-383.
Vainchenker et al., "JAKs in pathology: Role of Janus kinases in hematopoietic malignancies and immunodeficiencies", Seminars in Cell & Developmental Biology, 2008, vol. 19(4), pp. 385-393.
Verstovsek S., "Therapeutic Potential of JAK2 Inhibitors," Hematology Am. Soc. Hematol. Educ. Program, 2009, pp. 636-642.
Walsmith, "Tumor Necrosis Factor-a Production Is Associated with Less Body Cell Mass in Women with Rheumatoid Arthritis", J Rheumatol., vol. 31, 2004, pp. 23-29.
Wernig, "Efficacy of TG101348, a Selective JAK2 Inhibitor, in Treatment of a Murine Model of JAK2V617F-Induced Polycythemia Vera", Cancer Cell, vol. 13, No. 4, 2008, pp. 311-320.
Wieland, et al., "Osteoarthritis—An Untreatable Disease?," Nat Rev Drug Discov., vol. 4, No. 4, 2005, pp. 331-344.
Wirtz, "Mouse Models of Inflammatory Bowel Disease", Advanced Drug Delivery Reviews, vol. 59, 2007, pp. 1073-1083.
Xiang, "Identification of Somatic JAK1 Mutations in Patients with Acute Myeloid Leukemia", Blood, vol. 111, 2008, pp. 4809-4812.
Yoshida, et al., Biochem & Biophysical Res Commun., "Low dose CP-690,550 (tofacitinib, a pan-JAK inhibitor . . . ," 2012, vol. 418, pp. 234-240.
Yu, et al., "Influence of Drug Release Properties of Conventional Solid Dosage Forms on the Systemic Exposure of Highly Soluble Drugs," AAPS Pharmsci, vol. 3(3), 2001, pp. 86-92.
Zenz, et al., "Psoriasis-like Skin Disease and Arthritis Caused by Inducible Epidermal Deletion of Jun Proteins," Nature, vol. 437, 2005, pp. 369-375.
Zhang, et al., "Activation of Jak/STAT Proteins Involved in Signal Transduction Pathway Mediated by Receptor for Interleukin 2 in Malignant T Lymphocytes Derived from Cutaneous Anaplastic Large T-cell Lymphoma and Sezary Syndrome," Proc. Natl. Acad. Sci. USA, vol. 93, Aug. 1996, pp. 9148-9153.
Zikherman, et al., "Unraveling the Functional Implications of GWAS: How T Cell Protein Tyrosine Phosphatase Drives Autoimmune Disease", J Clin Invest., 2011, vol. 121, No. 12, pp. 4618-4621.

\* cited by examiner

METHODS FOR THE TREATMENT OF PSORIATIC ARTHRITIS

CROSS-REFERENCE TO RELATED APPLICATIONS

This application is a National Stage Entry of PCT/EP2019/063283, filed May 23, 2019, which claims foreign priority to GB Patent Application No. 1808575.3, filed on May 24, 2018, the disclosures of which are hereby incorporated by reference in their entireties.

FIELD OF THE INVENTION

The present invention relates to the medical use of the compound of the invention according to formula I for the treatment of Psoriatic Arthritis (PsA). The present invention also provides methods for the treatment and/or prophylaxis of PsA by administering the compound of the invention according to formula I.

BACKGROUND

Psoriatic arthritis (PsA) is an inflammatory form of arthritis, affecting up to 30 percent of psoriasis patients. Psoriatic arthritis can cause swelling, stiffness and pain in and around the joints, cause nail changes and overall fatigue. Studies show that delaying treatment for psoriatic arthritis as little as six months can result in permanent joint damage. Early recognition, diagnosis and treatment of psoriatic arthritis are critical to relieve pain and inflammation and help prevent joint damage. Despite the availability of a number of treatment options, few current treatments effectively relieve the enthesitis and symptoms in the joints and the skin.

In fighting RA, Janus kinase (JAK) inhibitors have been developed. JAKs are cytoplasmic tyrosine kinases that transduce cytokine signaling from membrane receptors to STAT transcription factors. Four JAK family members have been described, JAK1, JAK2, JAK3 and TYK2. Upon binding of the cytokine to its receptor, JAK family members auto- and/or transphosphorylate each other, followed by phosphorylation of STATs that then migrate to the nucleus to modulate transcription. JAK-STAT intracellular signal transduction serves the interferons, most interleukins, as well as a variety of cytokines and endocrine factors such as EPO, TPO, GH, OSM, LIF, CNTF, GM-CSF and PRL (Vainchenker et al., 2008).

JAK1 is a target in the immuno-inflammatory disease area. JAK1 heterodimerizes with the other JAKs to transduce cytokine-driven pro-inflammatory signaling. Therefore, inhibition of JAK1 is of interest for immuno-inflammatory diseases with pathology-associated cytokines that use JAK1 signaling, such as IL-6, IL-4, IL-9, IL-15, IL-21, or IFNγ, as well as for other diseases driven by JAK-mediated signal transduction. The compound according to formula I, cyclopropanecarboxylic acid {5-[4-(1,1-dioxo-thiomorpholin-4-ylmethyl)-phenyl]-[1,2,4]triazolo[1,5-a]pyridin-2yl}-amide (Compound 1), is disclosed in WO2010/149769 (Menet and Smits, 2010) and has the chemical structure shown below:

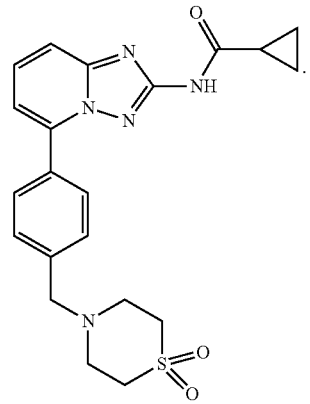

Compound I is a potent and selective inhibitor of JAK1, for the treatment of inflammatory disorders. Compound I is highly selective for inhibition of JAK1 among 451 unique kinase gene products tested in vitro. In a human whole-blood assay, cytokine-induced STAT1 phosphorylation was inhibited by compound I with half maximal inhibitory concentration ($IC_{50}$) values of 629 nM and 17,453 nM for JAK1 and JAK2-mediated signaling, respectively, demonstrating 27-fold selectivity for JAK1 over JAK2 in this assay. Compound I is thus a JAK1 selective inhibitor.

In humans, compound I is metabolized to form one major active metabolite, compound according to formula II:

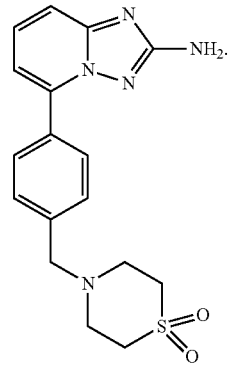

This molecule also inhibited JAK1 signaling, but was approximately 20-fold less potent and was about 10-fold more abundant than the parent compound. Though the potency of this metabolite is lower than the parent molecule, the overall exposure and peak plasma concentration in humans is higher than seen in all tested animal species. As a consequence, dedicated pharmacology and toxicology studies have been performed with compound II. Results from pharmacodynamics (PD) testing in healthy volunteers suggest that the clinical activity of compound I could result from the combination of the parent molecule and the metabolite. The compound according to formula II is described in WO2013/189771.

JAK inhibitors are evaluated for the treatment of PsA. A phase III trial in patients with active psoriatic arthritis who previously had an inadequate response to conventional synthetic disease modifying antirheumatic drugs, being administered tofacitinib showed an ACR20 response rate at month 3 of 50% dosed at 5 mg and 61% dosed at 10 mg compared to 33% in the placebo group (Mease P. et al NEJM 377; 161537-1550).

However, whereas JAK inhibitors are useful and effective molecules in the treatment of inflammatory conditions, drawbacks to the use of these compounds have been reported including anemia, thrombocytopenia and neutropenia, hypercholesterolemia, creatinine increase, all of which may result from the lack of selectivity, in particular selectivity against JAK2 (O'Shea, J. J. et al. 2013. Back to the Future: Oral targeted therapy for RA and other autoimmune diseases. Nat. Rev. Rheumatol. 9, 173-182; O'Shea, J. J., Plenge, R., 2012. JAKs and STATs in Immunoregulation and Immune-Mediated Disease. Immunity 36, 542-550). In contrast, selective JAK inhibition, in particular JAK1 may result in safe and effective treatment agent. (Yamaoka, K., 2016. Janus kinase inhibitors for rheumatoid arthritis. Curr. Opin. Chem. Biol. 32, 29-33).

Accordingly, there is still a need in the art for further agents in the treatment of PsA with a better risk-benefit profile.

SUMMARY OF THE INVENTION

The present invention relates to the finding that compound I has shown its unexpected high potential in treating psoriatic arthritis with a favorable benefit risk profile. In a Phase IIa trial (reported example 1 herein), an ACR20 of up to 80% following 16 weeks of using compound I in the treatment of patients suffering psoriatic arthritis is shown. Further particular findings will be apparent in the description of the invention below.

Accordingly, the present invention provides the compound according to formula I

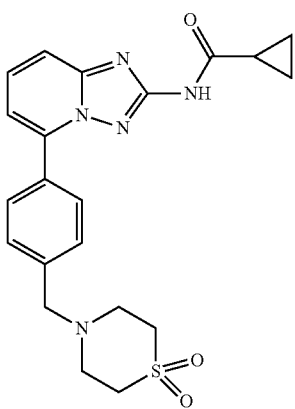

for use in the treatment of psoriatic arthritis dosed orally at a dose selected from 100 to 200 mg once a day, or 50 to 100 mg twice a day.

In a specific embodiment, the compound according to formula I is dosed as the sole active agent for the treatment PsA.

In a further embodiment is provided the compound according to formula I for use in the treatment of psoriatic arthritis dosed orally at a dose selected from 100 or 200 mg once a day, or 100 mg twice a day, where an ACR20 response is seen in at least 60, 70 or 80% of patients.

In a further embodiment is provided the compound according to formula I for use in the treatment of psoriatic arthritis dosed orally at a dose selected from 100 or 200 mg once a day, or 100 mg twice a day, where an ACR50 response is seen in at least 30, 35 or 40% of patients.

In a further embodiment is provided the compound according to formula I for use in the treatment of psoriatic arthritis dosed orally at a dose selected from 100 or 200 mg once a day, or 100 mg twice a day, where a statistically significant ACR20 response is seen following 1 week of treatment.

In a further embodiment is provided the compound according to formula I for use in the treatment of psoriatic arthritis dosed orally at a dose selected from 100 or 200 mg once a day, or 100 mg twice a day, where a statistically significant ACR50 response is seen following 1 week of treatment.

In a further embodiment is provided the compound according to formula I for use in the treatment of psoriatic arthritis in patients with enthesitis.

In a further embodiment is provided the compound according to formula I for use in the treatment of psoriatic arthritis in patients who were not previously exposed to bDMARDs, in particular anti-TNF pharmaceuticals.

In another embodiment is provided a composition, such as a pharmaceutical composition, comprising compound I according to any of the embodiments disclosed herein, and, a pharmaceutically acceptable vehicle.

In another aspect is provided a method of treatment of psoriatic arthritis comprising the step of administering a person in need thereof the compound according to formula I orally at a dose selected from 100 or 200 mg once a day, or 100 mg twice a day.

In an embodiment, the method of treatment leads to an ACR20 response in at least 60, 70 or 80% of patients. In a further embodiment, the ACR20 response is statistically significant following 1 week of treatment.

In another embodiment, the method of treatment leads to an ACR50 response in at least 30, 35 or 40% of patients. In a further embodiment, the ACR50 response is statistically significant following 1 week of treatment.

In a further embodiment, the patient subjected to the treatment was not previously exposed to bDMARDs, in particular to anti-TNF treatment.

In a further embodiment, the patient subjected to the treatment shows signs and/or symptoms of enthesitis.

DETAILED DESCRIPTION OF THE INVENTION

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles 'a' and 'an' may be used herein to refer to one or to more than one (i.e. at least one) of the grammatical objects of the article. By way of example 'an analogue' means one analogue or more than one analogue.

The terms 'compound I', 'compound according to formula I' or 'compound of formula I' may be used interchangeably to refer to the compound having structural formula I:

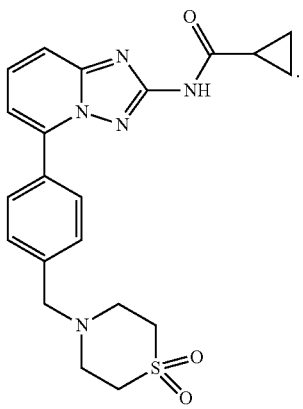

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g. an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. The term 'pharmaceutically acceptable cation' refers to an acceptable cationic counterion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Solvate' refers to forms of the compound that are associated with a solvent, usually by a solvolysis reaction. This physical association includes hydrogen bonding. Conventional solvents include water, EtOH, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Effective amount' means the amount of a compound of the invention that, when administered to a subject for treating a disease, is sufficient to effect such treatment for the disease. The "effective amount" can vary depending on the compound, the disease and its severity, and the age, weight, etc., of the subject to be treated.

'Preventing' or 'prevention' refers to a reduction in risk of acquiring or developing a disease or disorder, i.e. causing at least one of the clinical symptoms of the disease not to develop in a subject that may be exposed to a disease-causing agent, or predisposed to the disease in advance of disease onset.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Treating' or 'treatment' of any disease or disorder refers, in one embodiment, to ameliorating the disease or disorder (i.e. arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g. stabilization of a discernible symptom), physiologically, (e.g. stabilization of a physical parameter), or both. In a further embodiment, "treating" or "treatment" relates to slowing the progression of the disease.

For the purpose of the present invention, the terms "ACR20", "ACR50" and "ACR70" as used herein are scores which indicate how much a patient's symptoms of peripheral arthritis have improved according to criteria set out by the American College of Rheumatology (ACR). The ACR score represents a percentage. An ACR20 score means that a person's arthritis symptoms have improved by 20%, an ACR50 score means it has improved by 50%, and an ACR70 score means it has improved by 70%. Specifically, to qualify for an ACR20 score, a person must have at least 20% fewer tender joints (at least 20% improvement from baseline in tender joint counts, TJC68) and at least 20% fewer swollen joints (at least 20% improvement from baseline in swollen joint counts, SJC66). In addition the patient must show a 20% improvement in at least three of the following five areas: the person's overall (global) assessment of his or her own disease activity (on a 0-100 mm visual analog scale (VAS)), the physician's global assessment of the person's disease activity (on a 0-100 mm VAS), the person's assessment of his or her own PsA pain intensity (on a 0-100 mm VAS), the person's assessment of his or her own physical functioning as measured by HAQ-DI, and the results of a C-reactive protein (CRP) blood test (in mg/dL or mg/L). ACR50 and ACR70 scores use the same criteria but require 50% and 70% improvement, respectively.

As used herein, the term 'DAS28(CRP)' refers to a clinical scoring ranging from 2.0 to 10.0 to measure the disease activity in a patient, and includes a 28 tender and swollen joint count, CRP measurement from blood analysis, and a general health assessment on a VAS. Further details on the determination of DAS28(CRP) is provided in example 1. A DAS28(CRP) value below 2.6 is indicative of remission, a DAS28(CRP) between 2.6 and 3.2 is indicative of low disease activity, between 3.2 and 5.1 is indicative of moderate disease activity, whereas a DAS28(CRP) above 5.1 is linked to high disease activity (Wells et al., 2009 Ann. Rheum. Dis. 68, 954-960).

As used herein, the term 'CRP' refers to the C-Reactive protein in blood serum and is a marker of inflammation. In particular guidelines for CRP are widely available, and normal values of <0.5 mg/dL are recommended (Porter, 2011 The Merck Manual of Diagnosis and Therapy (Wiley)).

As used herein, the term 'enthesitis' refers to entheseal inflammation which is a typical feature of PsA and is one of the features which distinguishes it from rheumatoid arthritis.

As used herein, the term 'SPARCC Enthesitis Index' refers to a clinical scoring after examination of (entheseal) tenderness at 16 peripheral sites, which are evaluated for tenderness by palpation, and scored 0 (non-tender) or 1 (tender). The total enthesitis score is the sum of all site scores and is maximally 16. The higher the score, the higher the enthesitis burden. (Maksymowych W P et al. Development and validation of the Spondyloarthritis Research Consortium of Canada (SPARCC) Enthesitis Index. Ann Rheum Dis 2009; 68:948-53)

As used herein, the term 'Leeds Enthesitis Index' or 'LEI' refers to a clinical scoring after examination of (entheseal) tenderness at six sites: 2 sites at each of the lateral epicondyles of the humerus, medial condyles of the femur and the insertion of the Achilles tendon. The LEI score range is 0-6. The higher the score, the higher the enthesitis burden.

As used herein, the term 'HAQ-ID' refers to the Health Assessment Questionnaire without Disability Index, which is a measure for the physical functioning of a patient. The HAQ-DI is a 20-question instrument assessing the degree of difficulty a person has in accomplishing tasks in 8 function areas (B. Bruce and J. Fries, "The Stanford Health Assessment Questionnaire: dimensions and practical applications," Health Qual Life Outcomes, p. 1:20, 2003). The HAQ-DI total score ranges from 0 to 3 with higher scores indicating greater dysfunction.

As used herein, the term 'MDA' refers to the Minimal Disease Activity, which is a measure for disease remission. For the purpose of the present invention a patient will be classified as having achieved MDA when 5 out of 7 of the following criteria are met:
TJC68 ≤1
SJC66 ≤1
PASI ≤1 or BSA ≤3%
Patient's Global Assessment of PsA pain intensity score ≤15 (0-100 mm VAS)
Patient's Global Assessment of Disease Activity ≤20 (0-100 mm VAS)
HAQ-DI ≤0.5
SPARCC Enthesitis Index ≤1.

As used herein, the term 'PASI' refers to the Psoriasis Area and Severity Index score and is an index used to express the severity of psoriasis. It combines the severity (erythema, induration and desquamation) and percentage of affected area. Further details on the determination of PASI is provided in example 1. The PASI score represents the change from baseline. 'PASI50' refers to the portion of patients who achieved 50% improvement in the PASI score upon the tested treatment. 'PASI75' refers to the portion of patients who achieved 75% improvement in the PASI score upon the tested treatment. 'PASI90' refers to the portion of patients who achieved 90% improvement in the PASI score upon the tested treatment.

As used herein, the term 'BSA' refers to the body surface area and is an estimation of the percentage of the body affected by psoriasis. BSA <3% is scored mild case of psoriasis, BSA of 3-10% is scored as a moderate case of psoriasis, and BSA >10% is scored as a severe case of psoriasis.

As used herein, the term 'cDMARD' refers to conventional disease modifying anti rheumatic drugs. Typically, cDMARD are synthetic drug also referred to as conventional synthetic disease modifying anti rheumatic drugs (csDMARD). Specific examples of cDMARD for the treatment of psoriatic arthritis include methotrexate, leflunomide, sulfasalazine, chloroquine and hydroxychloroquine.

As used herein, the term 'bDMARD' refers to biological disease modifying anti rheumatic drugs. A particular class of bDMARDS are tumor necrosis factor (TNF) inhibitors, also referred to as anti-TNF pharmaceuticals, such as etanercept, adalimumab, infliximab, golimumab, certolizumab or certolizumab pegol.

As used herein the term 'TNF-naïve patient' refers to a patient previously not exposed to an anti-TNF pharmaceutical such as anti-TNF monoclonal antibody treatment or subjects previously exposed to anti-TNF therapy (for example and without limitation infliximab, golimumab, adalimumab, certolizumab and/or certolizumab pegol) at a dose registered for the treatment of inflammatory conditions that has been discontinued at least 8 weeks prior to entering the study.

As used herein the term 'TNF-experienced patient' refers to a patient that is receiving at the time of entering the study or has received anti-TNF pharmaceutical such as anti-TNF monoclonal antibody treatment (for example and without limitation infliximab, golimumab, adalimumab, certolizumab and/or certolizumab pegol) and is no longer responsive to such treatment.

As used herein the term 'anti-TNF pharmaceutical' refers a class of drugs that are used to treat inflammatory conditions, in particular rheumatoid arthritis (RA), psoriatic arthritis, juvenile arthritis, inflammatory bowel disease (Crohn's and ulcerative colitis), ankylosing spondylitis and psoriasis. TNF is a chemical produced by the immune system that causes inflammation in the body. In healthy individuals, excess TNF in the blood is blocked naturally, but in those inflammatory conditions, higher levels of TNF in the blood lead to more inflammation and persistent symptoms. Particular examples of anti-TNF pharmaceutical include infliximab, golimumab, adalimumab, certolizumab and certolizumab pegol. Accordingly, the term "anti-TNF treatment" refers to treatment by means of administering an anti-TNF pharmaceutical.

The term 'compound of the invention" and equivalent expressions, is meant to embrace the compound of formula I as herein described, which expression includes the pharmaceutically acceptable salts, and the solvates, e.g. hydrates, and the solvates of the pharmaceutically acceptable salts where the context so permits. Similarly, reference to intermediates, whether or not they themselves are claimed, is meant to embrace their salts, and solvates, where the context so permits.

The term 'treatment effect' refers to the effect attributed to a particular or specified treatment, such as treatment of psoriatic arthritis using compound I.

Psoriatic arthritis (PsA) is an inflammatory joint disease associated with psoriasis and characterized by heterogeneous musculoskeletal phenotypes that involve multiple domains including the peripheral joints, axial skeleton, tendon and ligament insertion sites (enthesitis) and digits (dactylitis). PsA occurs in approximately 30% of psoriasis patients. In the majority of cases (75%) psoriasis precedes joint disease, but in some cases (15%) the onset is synchronous and in 10% arthritis precedes psoriasis. In the latter, unrecognized psoriasis may be found or there may be a history of widespread guttate psoriasis in childhood or a strong family history.

PsA occurs just as frequently in males and females. The arthritis in PsA commonly involves distal joints and has the tendency to distribute in a ray pattern, so that all the same joints of a single digit are more likely to be affected (dactylitis). The degree of erythema over the affected joints, the presence of asymmetrical spinal involvement, the presence of enthesitis and a lower level of tenderness are also typical features of PsA. PsA belongs to the group of spondyloarthropathies because of the presence of spondylitis in up to 40% of patients. The extra-articular features observed in PsA are similar to other spondyloarthropathies including mucous membrane lesions, iritis, urethritis, diarrhea and aortic root dilatation, and association with HLA-B27.

First-line treatment traditionally consists of non-steroidal anti-inflammatory drugs (NSAIDs) and conventional disease-modifying anti-rheumatic drugs (cDMARDs) such as sulfasalazine (SSZ), methotrexate (MTX) and leflunomide (LEF). These drugs remain a mainstay of therapy where there is limited access to biological agents. The arrival of anti-tumor necrosis factor (anti-TNF) agents over a decade ago dramatically increased the treatment armamentarium for PsA leading to much improved outcomes for both skin and joint disease. Nevertheless, anti-TNF agents do not work in all patients and may lose response over time, partly because of immunogenicity. Agents with different mechanism of actions that target the interleukin(IL)-23/IL-17 pathways that promote skin and joint inflammation have become available and more are currently under evaluation in clinical studies. These agents include the IL-12/IL-23 inhibitors ustekinumab, and tildrakizumab; the IL-23 inhibitor guselkumab; the IL-17 receptor A inhibitors such as secukinumab and ixekizumab, the IL-17 receptor inhibitor brodalumab, the IL-17 receptor A/F inhibitor bimekizumab and the phosphodiesterase E4 inhibitor apremilast. The therapeutic response of these new agents is most evident in psoriasis, resulting in marked plaque clearance; the results in PsA for these agents are similar to those observed with anti-TNF agents. IL-17 blockade is also effective for axial disease and inhibits radiographic progression. The oral agent apremilast offers a modest response in the skin and joints, with few safety signals and is not indicated in patients who demonstrate radiographic damage or axial involvement.

Several key cytokines in the IL-23/IL-17 pathways promote skin and joint inflammation signal through the Janus Kinase (JAK) family of receptor-associated TYKs. Activated JAKs recruit and activate signal transducer and activator of transcription (STATs) which in turn drive gene transcription. The specific JAK-STAT activation depends on the cytokine signal which includes IFN and its related cytokines, the common γ-chain cytokines and the IL-6 type cytokines. Studies have demonstrated increased phosphoSTAT3 (pSTAT3) and pSTAT1 expression in psoriasis skin and have shown that IFNγ, IL-6 and IL-22 can induce pSTAT1 or pSTAT3 in keratinocytes.

INVENTION

The present invention provides the compound of the invention for use in the treatment of psoriatic arthritis, wherein the compound of the inventions is according to formula I:

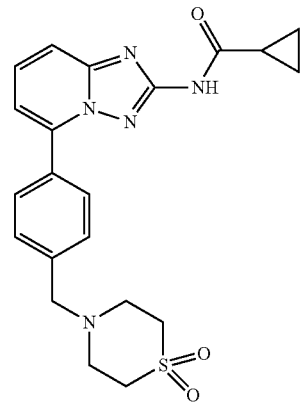

In one aspect a compound of the invention according to any one of the embodiments herein described is present as the free base.

In one aspect a compound of the invention according to any one of the embodiments herein described is a pharmaceutically acceptable salt. In a particular embodiment, the compound of the invention is present as a 1:1 maleate salt.

In one aspect a compound of the invention according to any one of the embodiments herein described is a solvate of the compound.

In one aspect a compound of the invention according to any one of the embodiments herein described is a solvate of a pharmaceutically acceptable salt of a compound. In a specific embodiment, the solvate of a pharmaceutically acceptable salt is a [Compound according to Formula I:HCl: $3H_2O$] adduct.

It will be appreciated that compounds of the invention may be metabolized to yield biologically active metabolites. An active metabolite of the compound according to formula I is described in WO2013/189771. In an alternative aspect, a compound of the invention is said metabolite of the compound according to Formula I, said metabolite being according to formula II:

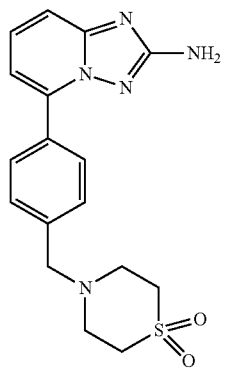

In one embodiment, the present invention provides the compound of the invention or pharmaceutical compositions comprising the compound of the invention, for use in the treatment of psoriatic arthritis when dosed orally at a daily dose of between 100 mg to 250 mg, administered in one or two gifts. In particular, the dose is selected from 50 mg twice per day (b.i.d.), 100 mg once a day (q.d.), 100 mg b.i.d., and 200 mg q.d.

In one embodiment, with respect to the uses and methods described above, the patients are not concomitantly treated with another agent or medicine for psoriatic arthritis.

In another embodiment, with respect to the uses and methods described above, the patients have had insufficient response to or are intolerant to one or more conventional Disease Modifying AntiRheumatic Drug (cDMARD), such as methotrexate, leflunomide, sulfasalazine and hydrochloroquine or chloroquine.

In an alternative embodiment, with respect to the uses and methods described above, the patients are concomitantly treated with another agent for the treatment of psoriatic arthritis, such as cDMARD therapy, such as treatment with methotrexate (such as up to 25 mg/week orally or parental), leflunomide (such as up to 20 mg/day orally), sulfasalazine (such as 3 g/day orally), hydrochloroquine (such as up to 400 mg/day) or chloroquine (such as up to 250 mg/day).

In another embodiment, with respect to the uses and methods described above, the patients are naïve to treatment with a bDMARD, in particular an anti-TNF pharmaceutical.

In an alternative embodiment, with respect to the uses and methods described above, the patients were previously treated with a bDMARD, in particular an anti-TNF pharmaceutical, and in particular, the patients had insufficient or inadequate response to previous treatment using a bDMARD such as an anti-TNF pharmaceutical.

In another embodiment, the compound of the invention is particularly useful for the treatment of a patient having psoriatic arthritis who displays signs and symptoms of enthesitis. In a further embodiment, such PsA patient suffers enthesitis as determined per SPARCC Enthesitis Index. In an alternative embodiment, such PsA patient suffers enthesitis as determined per Leeds Enthesitis Index (LEI score), e.g. LEI score of more than 0.5 or more than 1.0.

In a specific embodiment with respect to the uses and methods described above in psoriatic arthritis patients, an ACR20 response is seen in at least 50% of the patient population after 4 weeks of treatment. Particularly, an ACR20 response is seen in at least 55%, at least 60%, of the patient population after 4 weeks of treatment. Particularly the ACR20 response is seen after 8 weeks of treatment, after 12 weeks of treatment or after 16 weeks of treatment. Particularly, an ACR20 response is seen in at least 75%, at least 76%, at least 77%, at least 78%, at least 79%, at least 80%, at least 81%, at least 82%, at least 83% of the patient population after 12 weeks of treatment. Particularly, the ACR20 response of at least 75%, at least 76%, at least 77%, at least 78%, at least 79%, at least 80%, at least 81%, at least 82%, at least 83% is seen after 16 weeks of treatment.

In a specific embodiment with respect to the uses and methods described above in psoriatic arthritis patients, an ACR50 response is seen in at least 30% of the patient population after 12 weeks of treatment. Particularly, an ACR50 response is seen in at least 31%, at least 32%, at least 33%, at least 34%, at least 35%, at least 36%, at least 37%, at least 38%, at least 39%, at least 40%, at least 41%, at least 42%, at least 43%, at least 44%, at least 45% of the patient population after 16 weeks of treatment.

In a specific embodiment with respect to the uses and methods described above in psoriatic arthritis patients, an ACR70 response is seen in at least 10% of the patient population after 12 weeks of treatment. Particularly, an ACR70 response is seen in at least 11%, at least 12%, at least 13%, at least 14%, at least 15%, at least 16%, at least 17%, at least 18%, at least 19%, at least 20%, at least 21%, at least 22%, at least 23%, at least 24%, at least 25% of the patient population after 16 weeks of treatment.

In a specific embodiment with respect to the uses and methods described above in psoriatic arthritis patients, the LEI score is reduced by at least 0.8, at least 0.9, at least 1.0, at least 1.1, at least 1.2, at least 1.3, at least 1.4, at least 1.5, at least 1.6, at least 1.7, at least 1.8 or at least 1.9. Particularly, the LEI score is reduced by at least 1.5, more specifically following 16 weeks of treatment, following 12 weeks of treatment, following 8 weeks of treatment or even more specifically following 4 weeks of treatment.

In a specific embodiment with respect to the uses and methods described above in psoriatic arthritis patients, the HAQ-DI (relating to the physical functioning of the patient) upon treatment using compound I reduces by at least 0.35, at least at least 0.40, at least 0.43, at least 0.44, at least 0.45, at least 0.46, at least 0.47, at least 0.48, at least 0.49, at least 0.50, at least 0.51, at least 0.52, at least 0.53, at least 0.54, at least 0.55, or at least 0.57. Particularly, the HAQ-DI is reduced by at least 0.40 points following 4 weeks of treatment. Particularly, the HAQ-DI is reduced by at least 0.45 points following 12 weeks of treatment. Particularly, the HAQ-DI is reduced by at least 0.45 points following 8 weeks of treatment. Particularly, the HAQ-DI is reduced by at least 0.50 points following 16 weeks of treatment.

In a another embodiment with respect to the uses and methods described above in psoriatic arthritis patients, compound I was effective in reducing psoriatic skin manifestations, also referred to as psoriasis. Such effect is assessed and quantified by Psoriasis Area and Severity Index (PASI) (see section 1.5.3). In a further, the compound according to formula I is for use in a PsA patient having psoriasis, such as patients with at least 3% of their body surface area covered by psoriasis. In an alternative embodiment, compound I is used to improve the pruritic component of psoriasis.

In another embodiment with respect to the uses and methods described above in psoriatic arthritis patients, at least 15%, at least 17% or at least 20% of the patients achieved MDA status following 16 weeks of treatment, or more specifically, following 12 weeks of treatment.

EXAMPLES

The compound of the invention according to formula I has been extensively profiled, and data are disclosed in WO 2010/149769 (Menet and Smits, 2010). The synthesis of the salt and suitable formulations have been described in WO2015/117980, WO2015/117981 and in PCT/US2018/022027.

Similarly, the compound of the invention according to formula II has been extensively profiled, and data are disclosed in WO 2013/189771 (Van't Klooster et al., 2013).

Example 1. Clinical Study—Treatment of Subjects with Moderately to Severely Active Psoriatic Arthritis (ClinicalTrials.gov Identifier: NCT03101670)

a. Purpose of the Study

The primary objective of the study is to evaluate the effect of compound I compared to placebo on psoriatic arthritis as assessed by the ACR20 following 16 weeks of treatment.

Secondary Objectives of the study are:
to evaluate the effect of compound I compared to placebo on:
  the signs and symptoms of PsA, as assessed by the MDA.
  the signs and symptoms of peripheral arthritis, as assessed by the ACR50 and ACR70 response, DAS28(CRP), SDAI, CDAI, EULAR, PsARC, Physician's and Patient's Global Assessment of Disease Activity, Patient's Global Assessment of PsA pain intensity, 66/68-joint count and CRP measurements.
  psoriasis, as assessed by PASI, PASI50, PASI75, PASI90 and PASI100 (including body surface area [BSA]), Physician's and Patient's Global Assessment of psoriasis, mNAPSI and pruritus NRS.
  enthesitis, as assessed by SPARCC Enthesitis Index and Leeds Enthesitis index.
  dactylitis, as assessed by LDI.
  physical function, as assessed by HAQ-DI.
  fatigue and general quality of life, as assessed by FACIT-Fatigue, SF-36 and PsAID.
to evaluate the safety and tolerability of compound I.
Exploratory objectives of the study are:
to evaluate the effects of compound I on spinal symptoms, as assessed by BASDAI.
to evaluate the effects of compound I on all aspects of PsA, as assessed by PASDAS.
to characterize the population PK and PD of compound I and its active metabolite in this population.

1.2. Study Design

This is a multicenter, Phase 2, double-blind, placebo-controlled study in subjects with moderately to severely active PsA who have an inadequate response or are intolerant to conventional disease-modifying therapy. A total of approximately 124 subjects are randomized to one of 2 treatment arms in a 1:1 ratio:compound I 200 mg q.d. or matching placebo q.d. Randomization to treatment groups are stratified by current cDMARD use (yes or no) and prior anti-TNF pharmaceutical use (yes or no).

1.3. Study Population 1.3.1. Sample Size

A sufficient number of subjects will be screened to ensure that approximately 124 subjects with moderately to severely PsA will be randomized to compound I 200 mg or matching placebo.

1.3.2 Inclusion Criteria

Subjects who meet all of the following criteria are eligible for the study:
1. Male or female subjects who are ≥18 years of age, on the day of signing informed consent.
2. Diagnosis of PsA for at least 12 weeks prior to Screening, and currently meet Classification Criteria for Psoriatic Arthritis (CASPAR).
3. Have active PsA defined as ≥5 swollen joints (from a 66 swollen joint count [SJC]) and ≥5 tender joints (from a 68 tender joint count [TJC]) at Screening and Baseline (measurable dactylitis of a digit counts as a single swollen joint and if tender, then also a single tender joint).
4. Have had a history of documented plaque psoriasis or currently active plaque psoriasis
5. If using cDMARD therapy, subjects are only permitted to use one of the following drugs and must have been on it for 12 weeks prior to Screening, with a stable dose (including stable route of administration) for at least 4 weeks prior to Baseline:
  Methotrexate oral or parenteral up to 25 mg/week (local standard of care must be observed with regard to concomitant use of folic or folinic acid supplementation);
  Leflunomide up to 20 mg/day orally;
  Sulfasalazine up to 3 g/day orally;
  Hydroxychloroquine up to 400 mg/day or chloroquine up to 250 mg/day.
6. If using non-drug therapies (including physical therapies), these should be kept stable during Screening.
7. Male and female subjects of childbearing potential who engage in heterosexual intercourse must agree to use highly effective methods of contraception
8. Women of childbearing potential must have a negative serum pregnancy test at Screening and negative urine pregnancy test at Baseline.
9. Able and willing to sign the informed consent form (ICF) as approved by the Independent Ethics Committee (IEC). Written consent must be provided before initiating any screening evaluations. Subjects must have read and understood the ICF, must fully understand the requirements of the study, and must be willing to comply with all study visits and assessments.

1.3.3. Exclusion Criteria

Subjects meeting one or more of the following criteria cannot be selected for this study:
1. Use of any of the following treatments:
  Current use of high potency opioid analgesics (e.g. methadone, hydromorphone, morphine or oxycodone);
  Use of alkylating agents, e.g. chlorambucil or cyclophosphamide, at any time;
  Use of JAK inhibitors, investigational or approved, at any time, including compound I;
  Prior use of more than one TNF inhibitor (including proposed biosimilars with demonstrated equivalence to an approved TNF inhibitor for efficacy in a clinical study), at any time. Prior use of one TNF inhibitor is allowed, with the following minimum washout periods prior to Screening:
    i. Etanercept: 4 weeks
    ii. Adalimumab, certolizumab pegol, golimumab: 8 weeks
    iii. Infliximab: 12 weeks;
  Use of any other investigational or approved biologic immunomodulating agents not listed above including, but not limited to: cell depleting biologic agents (e.g., anti-CD20, CAMPATH, anti-CD4, anti-CD3), denosumab, anti-IL-6 (e.g. tocilizumab), anti-IL-17 (e.g. secukinumab, ixekizumab, brodalumab), anti- IL-12/IL-23 (e.g. ustekimumab), anti-IL-23 (e.g. tildrakizumab, guselkumab), rituximab at any time;

Any intramuscular or intravenous corticosteroid treatment within 4 weeks prior to Screening;

Use of oral steroids at a dose >10 mg/day of prednisone or prednisone equivalent or at a dose that hasn't been stable for at least 4 weeks prior to Baseline;

Any therapy by intra-articular injections (e.g. corticosteroid, hyaluronate) within 4 weeks prior to Screening;

Use of more than 1 NSAID or cyclooxygenase-2 (COX-2) inhibitor. If an NSAID or COX-2 inhibitor is used, it must not exceed maximum doses permitted as per local labeling and must have been used at a stable dose for at least 2 weeks prior to Baseline. In addition, subjects are permitted to take acetylsalicylic acid at a dose of ≤325 mg q.d. for cardiac prophylaxis;

Leflunomide, if being discontinued less than 12 weeks prior to Baseline or less than 4 weeks prior to Baseline if a washout procedure (e.g. cholestyramine) has been performed;

Any of the following systemic immunomodulating therapies within 4 weeks prior to Screening, including but not limited to: 6-mercaptopurine, azathioprine, cyclosporine or other calcineurin inhibitors (e.g. sirolimus, tacrolimus), dapsone, fumaric acid derivatives, gold therapy, MTX if being discontinued, mycophenolate, antimalarials (e.g., hydroxychloroquine, chloroquine) if being discontinued, SSZ if being discontinued, apremilast or thioguanine;

Ongoing use of prohibited psoriasis treatments/medications within the specified minimum washout periods prior to Baseline as follows:
  iv. Oral retinoids (including tazarotene) or vitamin D analogues: 4 weeks
  v. Phototherapy (UVA or UVB) with or without psoralens or self-treatment with sunbathing or tanning beds: 4 weeks
  vi. Any topical therapies including, but not limited to: alpha or beta hydroxy acids, anthralin, corticosteroids (except mild potency corticosteroids on face, scalp, axillary and genital area), >3% salicylic acid preps, retinoids including tazarotene, tar preps, or urea: 2 weeks;

Treatment with any potent P-glycoprotein (P-gp) inducer (e.g. carbamazepine, clotrimazole, cyclosporine, dexamethasone, phenothiazine, phenytoin, retinoic acid, rifampin, St. John's wort and venlafaxine). Potent P-gp inducers require washout of 3 weeks prior to Baseline;

Use of any investigational drug and/or device not already mentioned within 4 weeks or 5 half-lives prior to Screening, whichever is longer.

2. Known hypersensitivity to study drug ingredients.
3. Have undergone surgical treatment for PsA including synovectomy and arthroplasty in more than 3 joints and/or within the last 12 weeks prior to Screening.
4. History of major surgery (requiring regional block or general anesthesia) within the last 12 weeks prior to Screening or surgery planned during the study.
5. Have a diagnosis of any generalized musculoskeletal disorder, e.g., generalized osteoarthritis, or systemic inflammatory condition other than PsA such as, but not limited to, RA, juvenile chronic arthritis, ankylosing spondylitis, reactive arthritis, IBD-associated arthropathies, systemic lupus erythematosus, scleroderma, inflammatory myopathy, mixed connective tissue disease, overlap syndrome or systemic vasculitis. Gout is permitted if subject is well controlled on urate lowering therapy with no evidence of flare of disease in the last year and current uric acid level <7.0 mg/dL.
6. Presence of very poor functional status or unable to perform self-care.
7. Presence of active IBD requiring systemic or topical therapies, current peptic ulcer disease or prior history of severe diverticulitis (i.e. requiring hospitalization) or previous gastrointestinal perforation.
8. Significant medical conditions including, but not limited to the following: uncontrolled hypertension (≥160/95 mmHg), congestive heart failure (New York Heart Association status of class III or IV), uncontrolled diabetes, cerebrovascular accident, myocardial infarction, unstable angina, unstable arrhythmia or any other cardiovascular condition in the past 24 weeks prior to Screening, which, in the opinion of the investigator, would put the subject at risk by participating in the study.
9. History of malignancy or myelo- or lymphoproliferative disorder within the past 5 years prior to Screening (except for no more than 3 lifetime occurrences of adequately treated basal cell carcinoma of the skin or cervical carcinoma in situ that has been treated with no evidence of recurrence).
10. History of bone marrow or organ transplant.
11. Untreated or inadequately treated active or latent TB infection (LTBI) based on any of the following findings:
    positive QuantiFERON-TB Gold test result (Note: if QuantiFERON-TB Gold test result is indeterminate, it may be repeated once, and if indeterminate or positive on retest, subject is not eligible) or
    chest radiograph (posterior anterior view), taken within 12 weeks prior to or at Screening and read by a qualified radiologist or pulmonologist, with evidence of current active TB or old inactive TB or
    symptoms suggestive of clinically significant illness with TB in the 12 weeks before the initial study drug administration.

Subjects with adequate treatment of LTBI or active TB infection may be permitted into the study with sponsor approval; this treatment must be documented and is defined as:
  i. Subject previously treated for TB, i.e. if a subject has previously completed an adequate course of therapy for either latent (36 weeks of isoniazid or other acceptable regimen and lives in a location where rates of primary multi-drug resistant TB infections are <5%) or active (acceptable multi-drug regimen) TB, no QuantiFERON-TB Gold test needs to be obtained, but a chest radiograph must be obtained if not done so within 12 weeks before Screening or if results are not available at the investigational site.

Subject with newly identified LTBI, i.e. a subject who has a newly identified positive diagnostic TB test result (defined as any positive QuantiFERON-TB Gold test or an indeterminate test result on 2 separate QuantiFERON-TB Gold tests) for whom active TB has been ruled out including having a negative chest radiograph, and for whom appropriate treatment for LTBI has been initiated, continued for at least 4 weeks prior to the first study drug administration and if ongoing at Screening is planned to be continued during the study until completed. Adequate treatment for LTBI is defined according to United States (US) Centers for Disease Control guidelines.
12. Positive serology for human immunodeficiency virus (HIV) 1 or 2, hepatitis B virus (i.e. hepatitis B virus surface antigen [HBsAg] or core antibody [Ab] positive) or hepatitis C virus (HCV) (i.e. HCV Ab positive) or any history of infectious hepatitis from any cause with the exception of hepatitis A.
13. History of invasive or opportunistic infection (e.g. listeriosis, *pneumocystis* or histoplasmosis) or immunodeficiency syndrome.
14. Active infection that is clinically significant, as per judgment of the investigator, or any infection requiring hospitalization or treatment with intravenous anti-infectives within 30 days of Screening or any infection requiring oral anti-infective therapy within 14 days of Screening.
15. Currently on any therapy for chronic infection (such as *pneumocystis*, cytomegalovirus, herpes simplex, herpes zoster and atypical mycobacteria).
16. History of symptomatic herpes zoster or herpes simplex infection within 12 weeks prior to Screening or have history of disseminated or complicated herpes zoster infection (e.g. multidermatomal, ophthalmic, or CNS involvement) at any time.
17. History of disseminated *Staphylococcus aureus* infection.
18. History of an infected joint prosthesis with the prosthesis still in situ.
19. Administration of a live or attenuated vaccine within 12 weeks prior to Baseline.
20. History within the previous 2 years or current evidence of drug or alcohol abuse per investigator opinion.
21. If applicable to national or local legislation, history of being admitted to an institution under an administrative or court order.
22. Pregnant, breastfeeding or planning pregnancy while enrolled in the study or within 35 days after last dose of study drug.
23. Any condition including unstable concomitant medical conditions or active fibromyalgia that, based on the investigator's clinical assessment, makes the subject an unsuitable candidate for the study due to potential to confound risk benefit assessments.
24. Any condition or circumstances which, in the opinion of the investigator or sponsor, may make a subject unlikely or unable to complete the study or comply with study procedures and requirements.
Significant blood loss (>450 mL) or transfusion of any blood product within 12 weeks prior to Baseline.
The results of the following laboratory tests performed at the central laboratory at Screening meet any of the criteria below:
Hemoglobin <8.5 g/dL (International System of Units [SI]: <85 g/L);
White blood cells <3.0×103 cells/mm3 (SI: <3.0×109 cells/L);
Neutrophils <1.5×103 cells/mm3 (SI: <1.5×109 cells/L);
Lymphocytes <0.5×103 cells/mm3 (SI: <0.5×109 cells/L);
Platelets <100×103 cells/mm3 (SI: <100×109 cells/L);
Alanine aminotransferase (ALT) or aspartate aminotransferase (AST)≥1.5×ULN;
Total bilirubin level ≥2×ULN, unless the subject has been diagnosed with Gilbert's disease and this is clearly documented;
Creatinine clearance <40 mL/min by Cockcroft-Gault equation.

1.4. Efficacy Assessments

Efficacy assessments to estimate signs and symptoms of PsA and peripheral arthritis, psoriasis, enthesitis, dactylitis, spondylitis, and physical function are carried out at Baseline (Day 1) and at Weeks 1, 2, 4, 8, 12, 16, or at the early discontinuation visit (EDV) if applicable, unless otherwise noted. The individual components of the ACR response criteria are obtained at screening and throughout the study.

Additionally, at Baseline (Day 1) and at Weeks 4 and 16 (or at the EDV, if applicable) subjects are asked to complete the Functional Assessment of Chronic Illness Therapy Fatigue scale (FACIT-Fatigue) questionnaire, 36-item Short-form Health Survey (SF-36 survey) and Psoriatic Arthritis Impact of Disease (PsAID) questionnaire.

1.4.1. High Sensitivity Serum C-Reactive Protein

The subject's serum CRP are measured using a hsCRP test at the time points indicated in the study flow chart. Post-baseline CRP results are blinded to the investigator and the sponsor until database lock.

1.4.2 66/68-Joint Count

Each of 66 joints will be evaluated for swelling (SJC66) and each of 68 joints for tenderness (TJC68) at time points described in the protocol.

A joint assessor with adequate training and experience in performing joint assessments is designated at each investigational site to perform all joint assessments. The joint assessor is preferably be a rheumatologist; however, if a rheumatologist is not available, it should be a health care worker with at least 1 year experience in performing joint assessments. The assessor should remain the same throughout the study per subject, as much as possible. It is required that the designated joint assessor identifies an appropriate back-up assessor to provide coverage if the designated joint assessor is absent.

The 68 tender joint count should be done by scoring the presence or absence of tenderness as assessed by pressure and joint manipulation on physical examination.

Synovial fluid and/or soft tissue swelling but not bony overgrowth represents a positive result for swollen joint count evaluated in 66 joints.

1.4.3. Physician's Global Assessment of Disease Activity

Global assessment of the subject's arthritis disease activity is performed by the physician, having access to the joint assessments (Section 1.4.2). A perpendicular line is drawn on the visual analog scale (VAS), and with a ruler, the distance between the "no disease activity" anchor and the mark on the 10-cm line in mm (with the end indicating "extreme disease activity") is the score from 0-100.

1.4.4. Enthesitis Assessment

Enthesitis is assessed using the SPARCC Enthesitis Index. Sixteen body sites is evaluated for tenderness by palpation, and scored with 0 (non-tender) or 1 (tender). The total enthesitis score is the sum of all site scores and is maximally 16. The higher the score, the higher the enthesitis burden.

In addition to the 16 sites used to assess enthesitis when evaluating the SPARCC Enthesitis Index, medial femoral condyles (left and right) is also assessed and evaluated in a similar way as the other 16 sites to allow assessing the Leeds enthesitis index (LEI).

1.4.5. Dactylitis Assessment

Dactylitis is assessed by evaluation of the size and tenderness of all fingers and toes using the LDI. The LDI measures the ratio of the circumference of the affected digit to the circumference of the digit on the contra-lateral hand or foot using a Leeds Dactylometer. A dactylitic digit is defined by a minimum difference of 10%. If the contralateral digit is also dactylitic, a table of normative values based on population averages is used to provide the comparison. The ratio of circumference is multiplied by a binary tenderness score (0 for non-tender, 1 for tender). The results from each digit with dactylitis are then summed to produce a final score.

1.4.6. Psoriasis Area and Severity Index (PASI) Score Including Body Surface Area (BSA)

The PASI score is used to measure the severity and extent of psoriasis. Representative area of psoriasis is selected for each body region (head, arms, trunk and legs). The intensity of erythema, induration and desquamation of the psoriasis is assessed as none (0), mild (1), moderate (2), severe (3) or very severe (4).

A numerical score, ranging from 0 to 100%, will be used to measure the proportion of the subject's total BSA involved with psoriasis, as assessed by the investigator.

1.4.7. Physician's Global Assessment of Psoriasis

The Physician's Global Assessment of psoriasis is used to determine the subject's psoriasis lesions overall at a given time point. The subject's psoriasis disease activity is assessed by a physician, using a 6-point scale (see 1.5.1 below), which ranges from 0 (cleared) to 5 (severe).

1.4.8. Modified Nail Psoriasis Area and Severity Index (mNAPSI)

The mNAPSI will evaluate the severity of nail matrix psoriasis and nail bed psoriasis (Cassell S. et al. "The modified Nail Psoriasis Severity Index: validation of an instrument to assess psoriatic nail involvement in patients with psoriatic arthritis.," *J Rheumatol.*, pp. 34(1):123-9, 2007). Characteristics of nail matrix psoriasis include pitting, leukonychia, red spots in the lunula, and nail plate crumbling. Nail bed characteristics affected by psoriasis include oil-drop discoloration, onycholysis, nail bed hyperkeratosis, and splinter hemorrhages.

Each of the subject's nails is assessed for presence of any of the nail matrix and nail bed psoriasis features, taking into account the following abnormalities and rules:

The following abnormalities are graded on a scale from 0-3:
  Onycholysis and oil-drop (salmon patch) dyschromia (will be considered together).
  Nail pitting
  Nail plate crumbling.

The next 4 abnormalities are scored only by their presence or absence. The score of 1 indicates presence and the score of zero indicates no presence:
  Leukonychia
  Red spots in the lunula
  Nail bed hyperkeratosis
  Splinter hemorrhages.

Each finger will have a score between 0 and 14, and the total mNAPSI score ranges from 0 to 140.

1.4.9. Patient's Global Assessment of Disease Activity

The subject's global assessment of their arthritis disease activity is recorded on a 0 to 100 mm VAS. A perpendicular line is drawn on the VAS, and with a ruler, the distance between the beginning of the line and the mark on the 10-cm line in mm will be the score from 0-100. A score of 0 indicates "very well" and 100 indicates "very poor" to the question "Considering all the ways psoriatic arthritis affects you, how well are you doing today?".

1.4.10. Patient's Global Assessment of Psoriasis

The Patient's Global Assessment of psoriasis is a single-item, patient-completed assessment that is used to evaluate the overall extent of psoriasis-related cutaneous disease at a particular point in time using a 5-category scale ranging from "clear" (0 points—no psoriasis) to "severe" (4 points).

1.4.11. Patient's Assessment of PsA Pain Intensity

The patient's assessment of pain is performed using a 0-100 mm VAS ranging from "no pain" to "unbearable pain" after the question "Please indicate with a vertical mark (|) through the horizontal line the most pain you had from your psoriatic arthritis today". The length of the line from 0 to the patient's mark is recorded. This assessment should be completed before the joint examination. This pain score is also used to derive the ACR20/50/70.

1.4.12. Health Assessment Questionnaire-Disability Index (HAQ-DI)

The HAQ-DI is used to monitor the subject's self-assessed physical function or disability. This 20-question instrument assesses the degree of difficulty a person has in accomplishing tasks in 8 function areas (getting dressed, arising, eating, walking, sleeping, hygiene, reaching, gripping, errands and chores). Responses are scored on a 4-point Likert scale from 0, indicating no difficulty, to 3, indicating inability to perform a task in that area. The need for aids/devices or help from another person is also recorded. The HAQ-DI total score ranges from 0 to 3 with higher scores indicating greater dysfunction.

1.4.13. Bath Ankylosing Spondylitis Disease Activity Index (BASDAI)

Patient-reported disease activity of the subject is measured using BASDAI (Sieper J. et al. "The Assessment of SpondyloArthritis international Society (ASAS) handbook: a guide to assess spondyloarthritis.," Ann Rheum Dis., pp. 68 Suppl 2:ii1-44, 2009). This is a 6-item index (fatigue, spinal pain, peripheral arthritis, enthesitis, intensity and duration of morning stiffness) in which the items are recorded on a 0 to 10 NRS. The total score ranges from 0-10 and scores of 4 or greater suggest suboptimal control of disease.

1.4.14. Pruritus Numeric Rating Scale (Pruritus NRS)

The subject is, at each study visit, asked to complete an evaluation of pruritus using a visual rating scale with numbered intervals (integers). The subject rates the intensity of pruritus based on a recall period of 24 hours of the most severe episode of pruritus experienced during that time interval. The subjects are asked to rate their pruritus on a 0 (no itching) to 10 (worst possible itching) scale.

1.4.15. Functional Assessment of Chronic Illness Therapy Fatigue Scale (FACIT-Fatigue)

The FACIT-Fatigue scale (version 4) measures an individual's level of fatigue during their usual daily activities over the past week. It consists of 13 questions with a 7-day recall period on a 5-point Likert scale, with 0 indicating "not at all" and 4 indicating "very much". The total score ranges from 0 to 52. The higher the score, the better the quality of life.

1.4.16. 36-item Short-Form Health Survey (SF-36)

The health-related quality of life of the subject is assessed using the SF-36 (version 2, SF-36v2® Health Survey) with a 1-week recall period. This consists of 36 questions belonging to 8 domains in 2 components:
  Physical well-being: 4 domains: physical functioning (10 items), role physical (4 items), bodily pain (2 items), and general health perceptions (5 items).
  Mental well-being: 4 domains: vitality (4 items), social functioning (2 items), role emotional (3 items), and mental health (5 items).

The remaining item (health transition) is not part of the above domains, but is kept separately.

These scores are rescaled from 0 to 100 (converting the lowest possible score to 0 and the highest possible score to 100), with higher scores indicating a better quality of life.

1.4.17. Psoriatic Arthritis Impact of Disease Questionnaire (PsAID)

The PsAID questionnaire assesses the impact of PsA on people's lives. For the current study, the EULAR PsAID questionnaire PsAID9 for clinical trials is used. It is a 9-item questionnaire, where each item is scored between 0 and 10. All items are prioritized according to importance of the health domain it represents. The weight of each domain is taken into account in the total PsAID score. A higher score on the PsAID indicates more impact of the disease. A score below 4 out of 10 is considered a patient-acceptable status. A change of 3 or more points is considered a relevant absolute change.

1.5. Efficacy Analysis 1.5.1. ACR20/50/70

The signs and symptoms of peripheral arthritis are measured using ACR20/50/70. The ACR response is a measurement of improvement in multiple disease assessment criteria.

A positive ACR20 response is defined as at least 20% improvement from baseline in both swollen (SJC66) and tender (TJC68) joint counts, and at least 20% improvement in 3 or more of the following 5 criteria:

Patient's Global Assessment of Disease Activity (0-100 mm VAS)

Physician's Global Assessment of Disease Activity (0-100 mm VAS)

Patient's Global Assessment of PsA pain intensity (0-100 mm VAS)

Patient's assessment of physical function as measured by HAQ-DI

CRP in mg/dL or mg/L

A positive ACR50 and ACR70 response is derived from the definition of the ACR20, but requiring at least 50% and 70% improvement, respectively.

At week 16, a statistically significant difference in ACR20, ACR50 and ACR70 score for compound I versus placebo is achieved. ACR20 and ACR50 reach statistically significant difference from placebo as from week 1.

TABLE 1

| ACR20 | | | |
|---|---|---|---|
| | 200 mg compound I q.d. (n = 65) | placebo q.d. (n = 66) | P-value |
| Week 1 | 26.2% | 4.5% | 0.003 |
| Week 2 | 33.8% | 15.2% | 0.0123 |
| Week 4 | 61.5% | 18.2% | <0.0001 |
| Week 8 | 67.7% | 28.8% | <0.0001 |
| Week 12 | 83.1% | 36.4% | <0.0001 |
| Week 16 | 80.0% | 33.3% | <0.0001 |

TABLE 2

| ACR50 | | | |
|---|---|---|---|
| | 200 mg compound I q.d. (n = 65) | placebo q.d. (n = 66) | P-value |
| Week 1 | 6.2% | 0% | 0.0364 |
| Week 2 | 10.8% | 0% | 0.048 |

TABLE 2-continued

| ACR50 | | | |
|---|---|---|---|
| | 200 mg compound I q.d. (n = 65) | placebo q.d. (n = 66) | P-value |
| Week 4 | 20.0% | 0.83% | 0.0017 |
| Week 8 | 32.3% | 4.23% | 0.0007 |
| Week 12 | 41.5% | 7.34% | 0.0003 |
| Week 16 | 47.7% | 8.44% | <0.0001 |

TABLE 3

| ACR70 | | | |
|---|---|---|---|
| | 200 mg compound I q.d. (n = 65) | placebo q.d. (n = 66) | P-value |
| Week 1 | 1.5% | 0% | 0.3055 |
| Week 2 | 3.1% | 0% | 0.1448 |
| Week 4 | 7.7% | 0.27% | 0.0830 |
| Week 8 | 12.3% | 0.27% | 0.0125 |
| Week 12 | 10.8% | 2.38% | 0.2968 |
| Week 16 | 23.1% | 2.38% | 0.0037 |

No marked difference is observed between patients naïve to anti TNF pharmaceuticals and patient who previously received anti TNF treatment.

1.5.2 Minimal Disease Activity (MDA)

The disease activity in PsA will be measured using the MDA, which is a measure to indicate disease remission. The MDA is based on a composite score of 7 domains. A patient will be classified as having achieved MDA when 5 out of 7 of the following criteria are met:

TJC68 ≤1

SJC66 ≤1

PASI ≤1 or BSA ≤3%

Patient's Global Assessment of PsA pain intensity score ≤15 (0-100 mm VAS)

Patient's Global Assessment of Disease Activity ≤20 (0-100 mm VAS)

HAQ-DI ≤0.5

SPARCC Enthesitis Index ≤1

TABLE 4

| MDA | | | |
|---|---|---|---|
| | 200 mg compound I q.d. (n=65) | placebo q.d. (n = 66) | P-value |
| MDA week 12 | 21.5% | 10.6% | 0.0691 |
| MDA week 16 | 23.1% | 9.1% | 0.0212 |

No marked difference is observed between patients naïve to anti TNF pharmaceuticals and patient who previously received anti TNF treatment.

1.5.3. Psoriasis (PASI)

Four sites of affection, the head (h), upper limb (u), trunk (t) and lower limbs (l), are separately scored by using 3 parameters, erythema (E), induration (I) and desquamation (D), each of which is graded on a severity scale of 0 to 4 (0=none, 1=mild, 2=moderate, 3=severe and 4=very severe) (Section 1.4.6). The area-wise percentage involvement of the involved sites is calculated as: 1=less than 10% area; 2=10-29%; 3=30-49%; 4=50-69%; 5=70-89%; and 6=more than 90%. The final formula for PASI score is:

$$PASI = 0.1 \times (Eh+Ih+Dh) \times Ah + 0.2 \times (Eu+Iu+Du) \times Au + 0.3 \times (Et+It+Dt) \times At + 0.4 \times (El+Il+Dl) \times Al$$

The total PASI score ranges between 0 (no disease) and 72 (maximal disease), but is considered unreliable when BSA <3%. Therefore, the PASI is only analysed in the subpopulation of subjects with psoriasis involving ≥3% BSA at baseline.

The following PASI parameters can be derived:
PASI change from baseline
PASI 50% improvement (PASI50)
PASI 75% improvement (PASI75)
PASI 90% improvement (PASI90)
PASI 100% improvement or complete resolution of all disease (PASI100)

TABLE 5

| PASI | | | |
|---|---|---|---|
| | 200 mg compound I q.d. (n = 42) | placebo q.d. (n = 40) | P-value |
| PASI mean cfb W12 | −5.5 | −3.1 | 0.0427 |
| PASI mean cfb W16 | −6.3 | −3.2 | 0.0070 |

TABLE 6

| PASI75 | | | |
|---|---|---|---|
| | 200 mg compound I q.d. (n = 42) | placebo q.d. (n = 40) | P-value |
| PASI75 W12 | 33.3% | 12.5% | 0.0304 |
| PASI75 W16 | 45.2% | 15.0% | 0.0034 |

No marked difference is observed between patients naïve to anti TNF pharmaceuticals and patient who previously received anti TNF treatment.

1.5.4. Enthesitis

Enthesitis is assessed using the SPARCC Enthesitis Index and Leeds Enthesitis Index (LEI). The Enthesitis parameters are analyzed only in the subpopulation of subjects who have enthesitis at baseline (LEI >0). Analysis focusses on the changes from baseline.

Compound I improved enthesitis compared with placebo. Per SPARCC Enthesitis Index, of the 85 (65%) patients with enthesitis at baseline, the mean change from baseline at week 16 was greater for filgotinib compared with placebo (LS mean difference −1.4 [95% CI −2.6 to −0.1], p=0.0310). Resolution of enthesitis did not differ significantly between the two groups (treatment difference 12% [−6.5 to 31.0], p=0.1583).

When assessing according to LEI, 76 (58%) patients had enthesitis at baseline. The treatment effect is reported in Table 7. Enthesitis was resolved in more patients who received filgotinib than who received placebo (treatment difference 26% [95% CI 4.0-45.1], p=0.0059).

TABLE 7

| LEI score (change from baseline) | | | |
|---|---|---|---|
| | 200 mg compound I q.d. (n = 33) | placebo q.d. (n = 43) | P-value |
| Week 4 | −1.7 | −0.5 | 0.0003 |
| Week 8 | −2.1 | −0.9 | 0.0004 |
| Week 12 | −1.9 | −1.0 | 0.0201 |
| Week 16 | −1.8 | −0.7 | 0.0004 |

No marked difference is observed between patients naïve to anti TNF pharmaceuticals and patient who previously received anti TNF treatment.

1.5.5. Physical Function (HAQ-DI)

HAQ-DI is scored on a scale from 0 to 3 and changes from baseline are reported. A decrease by at least 0.22 points versus the baseline is considered clinically meaningful.

| HAQ-DI | | | |
|---|---|---|---|
| | 200 mg compound I q.d. (n = 33) | placebo q.d. (n = 43) | P-value |
| Week 1 | −0.19 | −0.09 | 0.0781 |
| Week 2 | −0.30 | −0.12 | 0.0078 |
| Week 4 | −0.44 | −0.13 | 0.001 |
| Week 8 | −0.50 | −0.13 | <0.001 |
| Week 12 | −0.53 | −0.28 | 0.0090 |
| Week 16 | −0.57 | −0.28 | 0.0009 |

No marked difference is observed between patients naïve to anti TNF pharmaceuticals and patient who previously received anti TNF treatment.

The invention claimed is:

1. A method for treating a patient diagnosed with psoriatic arthritis, comprising administering a compound according to formula I:

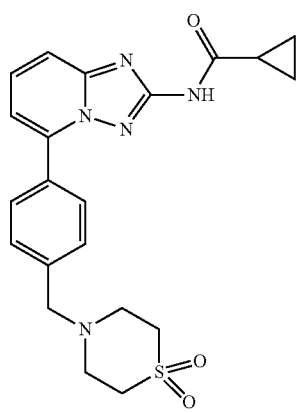

or a pharmaceutically acceptable salt thereof, or a solvate or the salt of a solvate thereof to the patient, wherein the compound is dosed at a daily dose of 100 to 200 mg, and wherein the patient has never been exposed to anti-TNF treatment or had an inadequate response prior to anti-TNF treatment, wherein the compound is dosed for a period of at least 16 weeks.

2. The method of claim 1, wherein the compound is dosed once (q.d.) or twice daily (b.i.d.).

3. The method of claim 1, wherein the treatment induces a treatment effect characterized by an American College of Rheumatology (ACR)20-score of at least 70%.

4. The method of claim 1, wherein the treatment induces a treatment effect characterized by an American College of Rheumatology (ACR50)-score of at least 40%.

5. The method of claim 1, wherein the patient diagnosed with psoriatic arthritis displays clinical signs and symptoms of enthesitis.

6. The method of claim 1, wherein the patient diagnosed with psoriatic arthritis has a Leeds Enthesitis Index (LEI) score of more than 0.

7. The method of claim 5, wherein the treatment induces a treatment effect characterized by a reduction of LEI score of at least 0.8.

8. The method of claim 1, wherein the treatment induces a treatment effect characterized by a reduction of Health Assessment Questionnaire without Disability Index (HAQ-DI) score of at least 0.35.

9. The method of claim 3, wherein the treatment effect is seen at week 12 of the treatment.

10. The method of claim 3, wherein the treatment effect is seen at week 16 of the treatment.

11. The method of claim 1, wherein the patient diagnosed with psoriatic arthritis displays more than 3% body surface area (BSA) psoriasis.

12. The method of claim 1, wherein the patient does not concomitantly receive any additional treatment for psoriatic arthritis, or, wherein the patient does not concomitantly receive any anti-TNF treatment.

\* \* \* \* \*